(12) United States Patent
Bechtel et al.

(10) Patent No.: US 8,620,682 B2
(45) Date of Patent: Dec. 31, 2013

(54) SMART CLINICAL CARE ROOM

(75) Inventors: Stephanie Palmer Bechtel, Overland Park, KS (US); Mark Nolte, Lee's Summit, MO (US); Eric Christian Kays, Olathe, KS (US); Scott Gordon Siebers, Leawood, KS (US); Gregory Ray Mitchem, Olathe, KS (US)

(73) Assignee: Cerner Innovation, Inc., Kansas City, MO (US)

(*) Notice: Subject to any disclaimer, the term of this patent is extended or adjusted under 35 U.S.C. 154(b) by 126 days.

(21) Appl. No.: 13/164,167

(22) Filed: Jun. 20, 2011

(65) Prior Publication Data
US 2012/0323591 A1 Dec. 20, 2012

(51) Int. Cl.
*G06Q 10/00* (2012.01)

(52) U.S. Cl.
USPC ............................................................ 705/2

(58) Field of Classification Search
USPC ............... 705/2, 3; 706/11, 12; 600/300, 301, 600/306, 509, 27
See application file for complete search history.

(56) References Cited

U.S. PATENT DOCUMENTS

| | | | |
|---|---|---|---|
| 4,669,263 A | 6/1987 | Sugiyama | |
| 5,592,153 A | 1/1997 | Welling | |
| 6,727,818 B1 | 4/2004 | Wildman et al. | |
| 7,015,816 B2 | 3/2006 | Wildman et al. | |
| 7,154,397 B2 | 12/2006 | Zerhusen et al. | |
| 7,237,287 B2 | 7/2007 | Weismiller et al. | |
| 7,408,470 B2 | 8/2008 | Wildman et al. | |
| 7,715,387 B2 | 5/2010 | Schuman | |
| 2006/0047538 A1 | 3/2006 | Condurso et al. | |
| 2006/0058587 A1 | 3/2006 | Heimbrock | |
| 2007/0120689 A1 | 5/2007 | Zerhusen et al. | |
| 2007/0136218 A1* | 6/2007 | Bauer et al. .................... 706/12 |
| 2008/0106374 A1 | 5/2008 | Sharbaugh | |
| 2009/0112630 A1 | 4/2009 | Collins et al. | |
| 2010/0169114 A1 | 7/2010 | Henderson et al. | |
| 2010/0169120 A1 | 7/2010 | Herbst | |
| 2011/0054936 A1 | 3/2011 | Cowan | |
| 2011/0068930 A1 | 3/2011 | Wildman et al. | |
| 2011/0077965 A1 | 3/2011 | Nolte | |
| 2011/0106560 A1 | 5/2011 | Eaton, Jr. | |
| 2011/0106561 A1 | 5/2011 | Eaton, Jr. et al. | |

OTHER PUBLICATIONS

Pre-Interview First Action Interview in U.S. Appl. No. 13/235,837 mailed May 23, 2013, 10 pages.

* cited by examiner

*Primary Examiner* — Lena Najarian
*Assistant Examiner* — Natalie A Pass
(74) *Attorney, Agent, or Firm* — Shook Hardy & Bacon LLP

(57) ABSTRACT

Methods, computer systems, and computer readable media for transitioning a clinical care room from a first scene to a second scene in order to facilitate completion of a real-world activity are provided. The first scene in the clinical care room is presented where the clinical care room has one or more zones. The first scene is associated with a first group of setting for components within the one or more zones. An input corresponding to the real-world activity is received. Incident to receiving the input, the second scene is provided. The second scene is associated with a second group of settings for the components. The second group of setting is optimized to facilitate completion of the real-world activity.

13 Claims, 14 Drawing Sheets

FIG. 7C.

SMART CLINICAL CARE ROOM

BACKGROUND

Traditionally, clinicians have to move through multiple parts of a hospital room to obtain needed equipment or supplies, and patients find themselves in an often unwelcoming and intimidating environment that lacks many of the comforting features they find at home. In addition, friends and members of the patient's family often find themselves in the way of the clinician while trying to visit the patient. The room layout does little to foster the required collaborative healthcare relationship among patient, clinician, and family.

In addition, many of the components present in the hospital room operate independently of each other. It is often the caregiver's responsibility to provide the needed integration by taking the results generated from one piece of equipment and manually inputting them into another piece of equipment or information system. The consequence of this is a lag in time between when the results are actually generated and when they are available to be used in the care of the patient, and general disorganization of the care experience for all stakeholders.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Embodiments of the present invention are directed to methods, computer systems, and computer-readable media for use in adaptively utilizing components present in a clinical care room to facilitate caring for a patient. This new generation smart room is designed in such a way as to create different zones within and outside the room with each zone taking advantage of certain components in support of specific workflows. In turn, the components in the room are integrated with each other and are contextually aware of each other. The end result is a room that can adaptively and automatically transform from one scene to another scene in order to meet the needs of clinicians, patients and family members.

BRIEF DESCRIPTION OF THE DRAWINGS

Embodiments are described in detail below with reference to the attached drawing figures, wherein:

FIGS. 7A-7C depict exemplary graphical user interfaces generated by a clinician dashboard component suitable to implement embodiments of the present invention;

DETAILED DESCRIPTION

Figure 1:
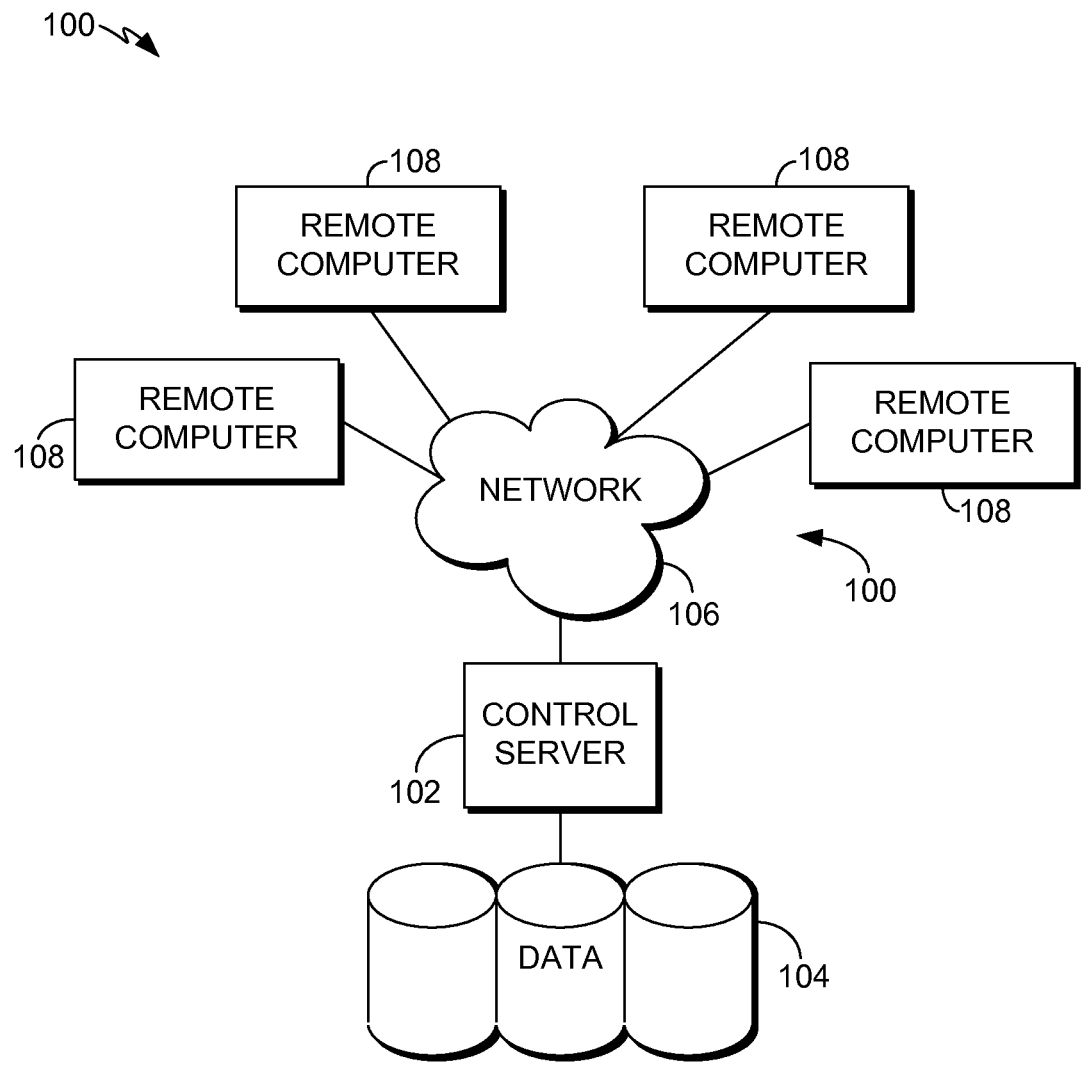
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

Examples of the present invention are directed to methods, computer systems, and computer-readable media for use in adaptively utilizing components present in a clinical care room to facilitate caring for a patient. This new generation smart room is designed in such a way as to create different zones within and outside the room with each zone taking advantage of certain components. In turn, the components in the room are integrated with each other. The end result is a room that can adaptively and automatically transform from one scene to another scene in order to meet the needs of clinicians, patients and family members. The term automatically can mean without human intervention.

Components may include any device or apparatus that impacts patient clinical care or manipulates the clinical environment in the clinical care room. As well, components may include any software module that provides instruction to other components. Components may also include such things as lights, television, sound system, furniture, and the like. As mentioned, the components may be integrated or related to each other.

One embodiment of the present invention is directed towards computer-readable storage media having embodied thereon computer-useable instructions which, when executed by a computing device, cause the computing device to perform a method for adaptively utilizing a clinical care room to facilitate caring for a patient. The method comprises receiving an input indicating a code blue event has been initiated for the patient. Incident to receiving the input, a clinical care team is notified of the code blue event, and one or more environmental conditions are modified in the clinical care room to facilitate patient care. Clinical event information related to the clinical care room and the patient is captured, and a code blue care plan is displayed to the clinical care team. The clinical event information is utilized to adaptively update the code blue care plan.

Another aspect of the present invention is directed towards computer-readable storage media having embodied thereon computer-useable instructions which, when executed by a computing device, cause the computing device to perform a method for transitioning a clinical care room from a first scene to a second scene to facilitate completion of a real-world activity. The first scene in the clinical care room is presented. The clinical care room has one or more zones, and the first scene is associated with a first group of settings for components within the one or more zones. An input is received corresponding to the real-world activity. Incident to receiving the input, the second scene is provided; the second scene is associated with a second group of settings for the components within the one or more zones. The second group of setting is different than the first group of settings, and the second group of settings is optimized to facilitate completion of the real-world activity.

The present invention also relates to computer-readable storage media having embodied thereon computer-useable instructions which, when executed by a computing device, cause the computing device to perform a method for adaptively utilizing a clinical care room to facilitate caring for a patient experiencing a code blue event. An input is received indicating that the patient is experiencing the code blue event. Incident to receiving the input indicating the code blue event, a code blue team is notified, and one or more environmental conditions in the clinical care room are modified to facilitate patient care. The modifications include adjusting room lighting and adjusting acoustic outputs in the clinical care room. One or more physical structures in the clinical care room are modified including adjusting the position of a patient bed.

Continuing with this aspect of the invention, clinical event information related to the clinical care room and the patient is captured. The clinical event information includes at least one of: a presence and position of members of the clinical care team, a time at which clinical events occur, medications administered to the patient, vital signs associated with the patient, lab results associated with the patient, and procedures performed on the patient. A code blue care plan is displayed to the code blue team, and the clinical event information is utilized to adaptively update the code blue care plan. Advice is also displayed related to the next step in the code blue care plan.

Having briefly described embodiments of the present invention, an exemplary operating environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. Computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including database cluster 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. In this regard, computer-readable media might comprise RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. The computer-readable media discussed provide storage of computer-readable instructions, data structures, program modules, and other data for the control server 102. Computer-readable media are non-transitory. Combinations of any of the above also may be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The peer devices can be personal digital assistants, smart phones, tablet PCs, personal computers, or other like devices.

Exemplary computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the database cluster 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
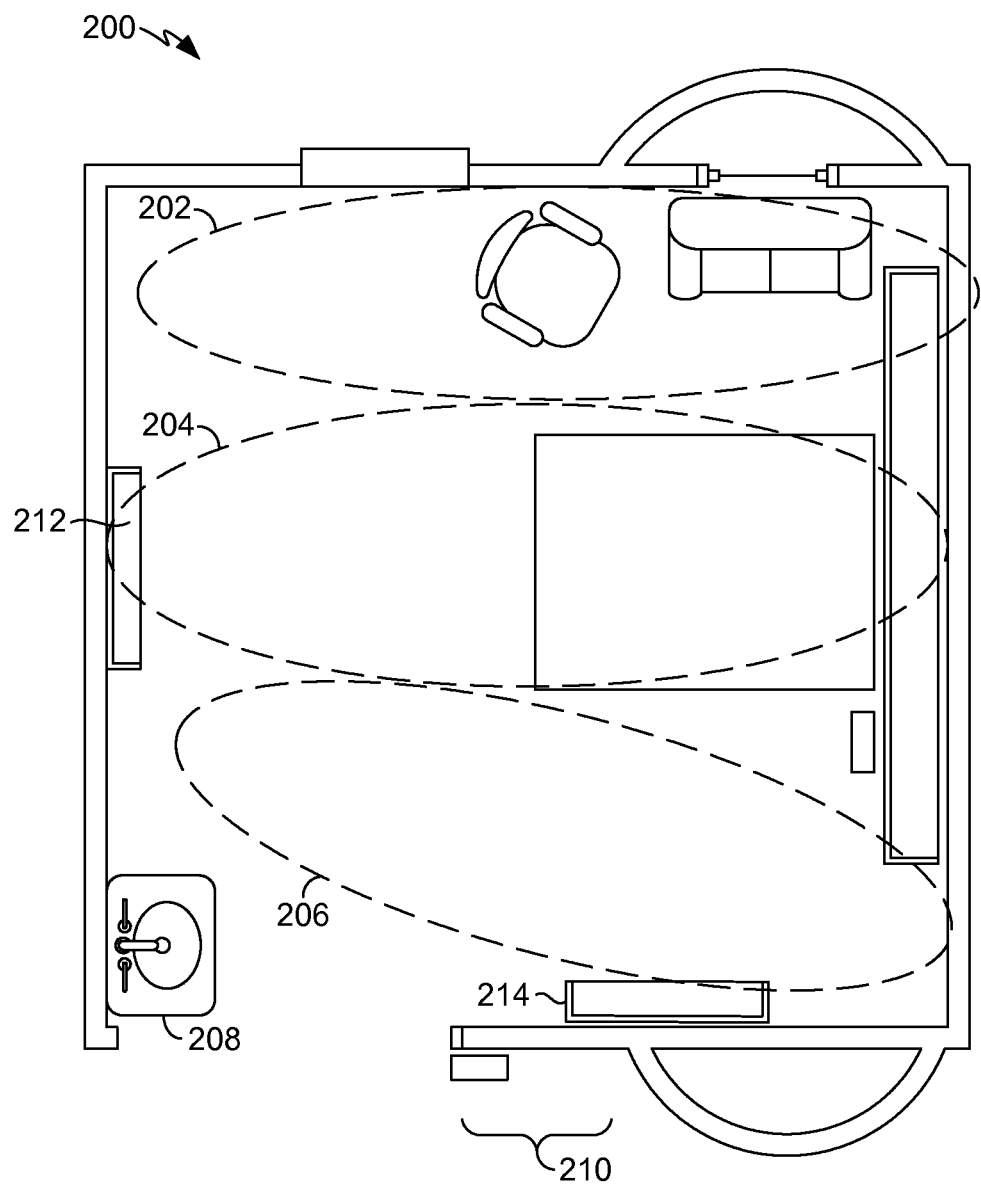
FIG. 2 depicts an exemplary layout of a smart clinical care room suitable to implement embodiments of the present invention.

Turning now to FIG. 2, an exemplary layout of a smart clinical care room 200 is depicted. FIG. 2 is merely one example of a suitable layout and is not intended to suggest any limitation as to the scope of use or functionality of the invention. In one aspect, smart clinical care room 200 is divided into three zones: a family/friend zone 202, a patient zone 204, and a clinician zone 206. The zones 202, 204, and 206 may be completely distinct from one another as shown in FIG. 2, or the zones 202, 204, and 206 may overlap. If two of the zones overlap, the area of overlap may be thought of as a conversion zone that combines features of both zones. As well, areas of overlap may support processes related to both zones depending on the individual situation.

Family/friend zone 202 is designed to be welcoming to the patient's family and/or friends and to help make them part of the patient's healthcare experience. As such, in one aspect, family/friend zone 202 is situated to be close to the patient yet out of a clinician's way. Comfortable furniture is provided that can easily be moved if more space in the room is needed. In one aspect, the furniture is designed to automatically fold up upon detection of a triggering event and upon determining that no one is sitting on the furniture. For example, upon detection of a code blue event, the furniture automatically folds up to create more room for clinicians. In yet another aspect, the family/friend zone 202 includes a television and a work area with phone and internet access (not shown) so family members can remain productive while still providing valuable support to the patient. Additionally, in still another aspect, the family/friend zone 202 includes a small suite adjacent to the smart clinical care room 200 with its own bed, shower, television, and work area (not shown). The family/friend zone 202 includes components that allow family members or friends to control their own television, lighting, and the like. Any and all such variations, and any combination thereof, are contemplated to be within the scope of embodiments of the present invention.

The patient zone 204 is generally located in the center of the smart clinical care room 200 between the family/friend zone 202 and the clinician zone 206. The patient zone 204 is where the care of a patient mainly takes place. The patient zone 204 includes certain components, including a bed, that allow the patient to manage aspects of the smart clinical care room 200. As well, certain components in the patient zone 204 assist the patient in becoming an active healthcare participant. These components are explained in greater depth below. The wall located at the head of the patient's bed is known as the head wall, while the wall at the foot of the patient's bed is known as the foot wall. In one aspect, a patient interactive station 212 (discussed in more detail later) is located on the foot wall within easy viewing distance of the patient.

Clinician zone 206 is designed to enhance a clinician's workflow as the clinician interacts with the patient and the patient's family and friends. It is generally positioned close to the entrance of the smart clinical care room 200. A sink for washing hands, and materials and equipment needed to care for the patient, are located within the clinician zone 206. The positioning of the sink and supplies reduces the number of areas the clinician contacts while in the room, which, in turn, reduces the spread of nosocomial infections. In addition, fatigue is reduced by decreasing the number of steps the clinician must travel within the smart clinical care room 200. In one aspect, a clinician-dashboard display device 214 (discussed in more detail later) is located on a wall in the clinician zone 206 within easy viewing distance of the clinician and the patient.

Although not all are depicted in FIG. 2, the smart clinical care room 200 may also include a number of other zones. By way of example, the smart clinical care room 200 may include a bathroom zone (not shown). With respect to the bathroom zone, a bathroom is located close to the patient's bed and has good lighting. As well, a clear path with railings is provided between the patient's bed and the bathroom. The bathroom may be equipped with sensors that can determine how long a patient has been in the bathroom and whether the patient has fallen while in the bathroom. Alerts may be automatically sent to a nurse if the patient has fallen or is in the bathroom for an inordinate amount of time.

The smart clinical care room 200 may also include a sanitizing zone 208 both outside the entrance to the smart clinical care room 200 (not shown) and within the smart clinical care room 200. The sanitizing zone 208 outside the entrance to the smart clinical care room 200 includes a hand-hygiene center that dispenses antiseptic hand rubs. The sanitizing zone 208 in the smart clinical care room 200 is located close to the entrance of the room within the clinician zone 206. This zone may include a sink with a timer so that clinicians, family members, and friends wash their hands for an appropriate length of time, an automatic dispenser of antiseptic handwash products, an automatic paper towel dispenser, a glove dispenser, a hands-free trash receptacle, and educational materials regarding the efficacy of hand-washing in the prevention of disease. Antiseptic towelettes may be provided in the sanitizing zone 208 so that clinicians can wipe down equipment moveable from room to room such as, for example, stethoscopes. In addition, the sanitizing zone 208 in the smart clinical care room 200 may be equipped with sensors to detect the presence and identity of people at the sanitizing zone 208 and, in one aspect, to send alerts to the patient or clinician that proper handwashing has not taken place. In another aspect, upon detection of a presence at the sanitizing station, the water automatically turns on and the timer automatically starts. Any and all such variations, and any combination thereof, are contemplated to be within the scope of embodiments of the present invention.

The smart clinical care room 200 may also include a pre-room entrance zone 210, which contains the sanitizing zone 208 mentioned above along with room signage (discussed in more detail below) that delivers important information regarding the patient and/or the smart clinical care room 200.

A team zone and an operational zone may be located outside of the smart clinical care room 200. Although located outside the room, these zones have the ability to communicate and interact with the smart clinical care room 200. For example, an action taken in either the team zone or the operational zone may influence components present in the smart clinical care room 200. The team zone may be utilized in an intensive care environment where space is limited in the smart clinical care room 200. In this scenario, the team zone is located in front of a glass observation window. The zone is designed to allow multiple members of a clinical care team to congregate, view the patient through the glass observation window, view important information regarding the patient without disturbing the patient or the patient's family, and take actions that influence the components present in the smart clinical care room 200.

The operational zone is typically located at what is traditionally known as the nursing station. In one aspect, actions taken in the operational zone may influence components present in the smart clinical care room 200. The operational zone may include one or more display boards that display information not only about the patient and the smart clinical care room 200, but also about patients and components in other clinical care rooms, including smart clinical care rooms. The display boards may display information related solely to the patient in the smart clinical care room 200 upon detecting the presence of a clinician involved in the patient's care. Any and all such variations, and any combination thereof, are contemplated to be within the scope of embodiments of the present invention.

Figure 3:
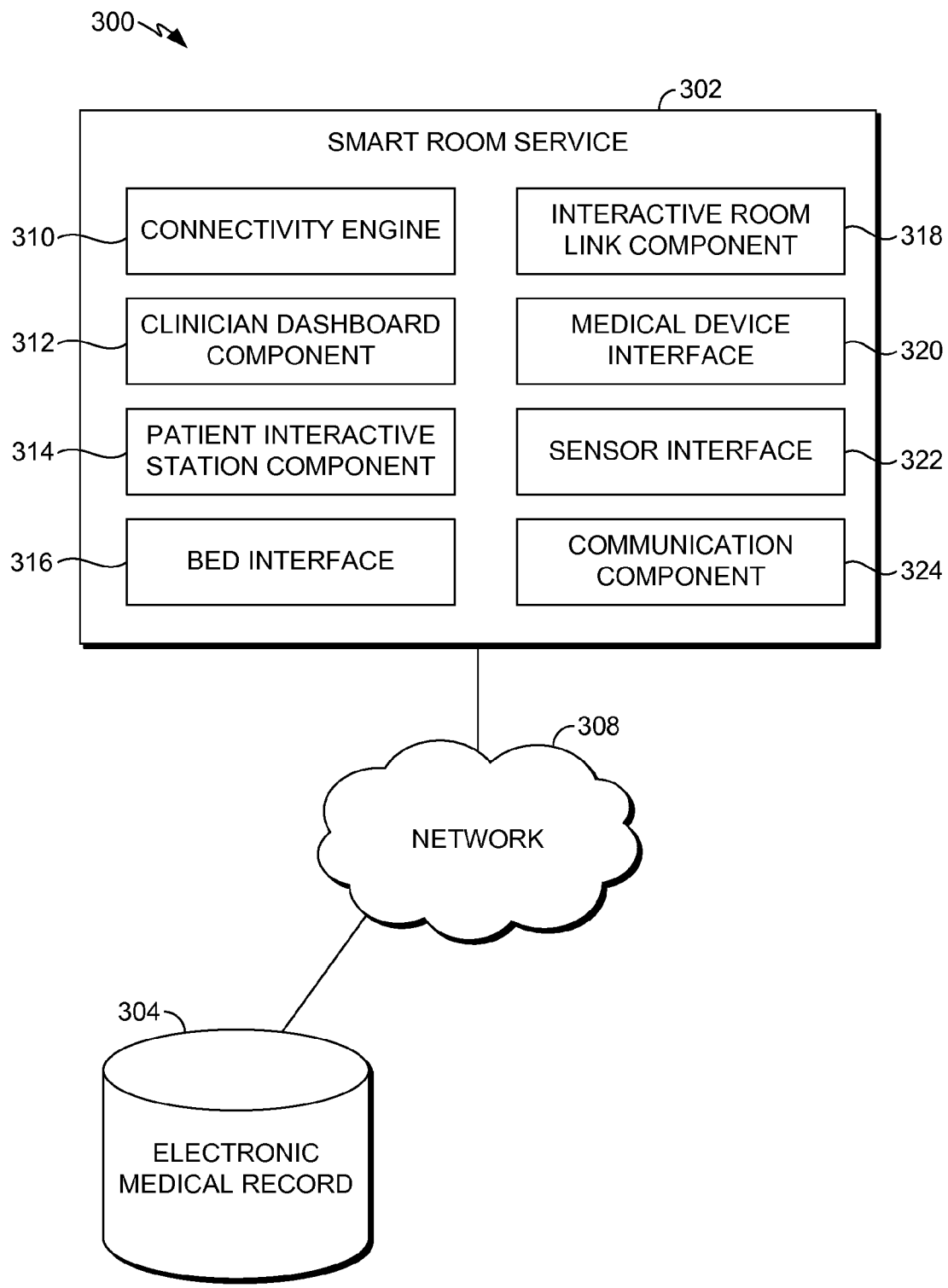
FIG. 3 is a block diagram of an exemplary computing system environment suitable for managing a smart clinical care room in accordance with an embodiment of the present invention.

Turning now to FIG. 3, a block diagram of an exemplary computing system environment 300 suitable for managing a smart clinical care room is depicted. It will be understood that the computing system environment 300 shown in FIG. 3 is merely an example of one suitable computing system environment for use with embodiments of the present invention. Neither should the computing system environment 300 be interpreted as having any dependency or requirement related to any single module/component or combination of modules/components illustrated therein. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The computing system environment 300 includes a smart room service 302, and an electronic medical record (EMR) 304 all in communication with one another via a network 308. The network 308 may include, without limitation, one or more local area networks (LANs) and/or wide area networks (WANs). Such networking environments are commonplace in offices, enterprise-wide computer networks, intranets and the Internet. Accordingly, the network 308 is not further described herein.

The EMR 304 comprises electronic clinical documents such as images, clinical notes, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

The smart room service 302 shown in FIG. 3 integrates the components in the room with each other. The smart room service 302 may work with any type of computing device, such as, for example, control server 102 or remote computer 108, described with reference to FIG. 1.

The computing system environment 300 is merely exemplary. While the smart room service 302 is illustrated as a single unit, one skilled in the art will appreciate that the smart room service 302 is scalable. For example, the smart room service 302 may in actuality include a plurality of computing devices in communication with one another. The single unit depictions are meant for clarity, not to limit the scope of embodiments in any form.

As shown in FIG. 3, the smart room service 302 comprises a connectivity engine 310, a clinician dashboard component 312, a patient interactive station component 314, a bed interface 316, an interactive room link component 318, a medical device interface 320, a sensor interface 322, and a communication component 324. In some embodiments, one or more of the components and/or interfaces 310, 312, 314, 316, 318, 320, 322, and 324 may be implemented as stand-alone applications. In other embodiments, one or more of the components and/or interfaces 310, 312, 314, 316, 318, 320, 322, and 324 may be integrated directly into the operating system of a computing device such as the computing environment 100 of FIG. 1. In addition, one or more of the components and/or interfaces 310, 312, 314, 316, 318, 320, 322, and 324 may be integrated directly into the electronic medical record 304. The components and/or interfaces 310, 312, 314, 316, 318, 320, 322, and 324 illustrated in FIG. 3 are exemplary in nature and in number and should not be construed as limiting. Any number of components may be employed to achieve the desired functionality within the scope of embodiments hereof.

The connectivity engine 310 is connected to the components and/or interfaces 312, 314, 316, 318, 320, 322, and 324 either wirelessly or via a wired connection. The connectivity engine 310 interacts with multiple medical devices and their attendant workflows. In one aspect, the connectivity engine 310 is designed to have a touch screen and be interactive. The connectivity engine 310 displays, upon a prompt by a clinician, a list of medical devices that are available to connect with. The connectivity engine 310 also communicates with the medical device interface 320 to capture outputs from medical devices such as, for example, vital sign capture. The connectivity engine 310 also communicates with the medical device interface 320 to associate a medical device with a patient—a process that will be explained in greater detail below. The connectivity engine communicates captured data to the EMR 304.

In one embodiment of the invention, the connectivity engine 310 is able to connect to medical devices via the medical device interface 320 in the following categories: anesthesia, balloon pumps, beds, blood bank, chemistry, coagulation, communication, dialysis, fetal monitoring, hematology, imaging, laboratory automation, medication dispensing, microbiology, nurse call, ophthalmology, patient monitoring, point of care, pulse oximeters, respiratory, smart pumps, ultrasound, urinalysis, ventilators, and patient monitoring devices. This list is not meant to be exhaustive or limiting in any manner.

The connectivity engine 310 may be communicatively coupled to various medical devices through either are wired or wireless connection. In one embodiment, a computing device associated with the connectivity engine 310 is located near the medical devices. In one aspect, this location is on the headwall near the patient. In another aspect, the connectivity engine 310 is integrated into a patient's bed. In another embodiment, the connectivity engine 310 runs on a computing device (e.g., PDA, tablet PC) that is used to display data from the medical devices and/or other component/interfaces of smart room service 302.

The connectivity engine 310 also assists in detecting types of medical devices so that the appropriate driver may be loaded, which may be based on the make and model of the particular medical device. The medical device interface 320 or a component thereof communicates with the connectivity engine 310 to establish a connection to the medical device itself. In one embodiment, the connectivity engine 310 is physically present in a patient's room so that when a new medical device is brought into that room, it is connected to the connectivity engine 310 if needed. At that time, a connect event may occur, and, for example, the medical device interface 320 and/or the connectivity engine 310 broadcasts the connect event to other components who may need to know.

The clinician dashboard component 312 is a control panel that processes clinical information and drives relevant content to a clinician-dashboard display device. The clinician-dashboard display device, in turn, may comprise cathode ray tubes (CRT) systems, plasma screens, liquid crystal display (LCD) systems, rear projection systems, light emitting diode (LED) systems, organic light emitting diode (OLED) systems, and the like. Clinician dashboard component 312 processes and generates relevant content in the form of lab results, workflows, medications, orders, vital signs, allergies, notes, consult notes, patient information, a location of the patient if the patient is not currently in the room, and the like. In one aspect, the relevant content may be displayed on the clinician-dashboard display device in the form of a graphical user interface (GUI).

The clinician dashboard component 312, in one aspect, communicates with the sensor interface 322 to detect the presence and identity of a clinician in the room through the use of, for example, radio-frequency identification tags worn by the clinician. This ability to detect the presence and identity of a clinician can be leveraged to display clinical information that is particularly relevant to the identified clinician. By way of illustrative example, if the clinician is identified as a respiratory therapist, the clinician dashboard component 312 generates display information that is relevant to the respiratory therapist. In one aspect, the clinician dashboard component 312 generates a team view when multiple members of a clinical care team are present in the patient's room. The clinical information that is subsequently displayed on the clinician-dashboard display device is relevant to the clinical care team as a whole.

The clinician dashboard component 312 may be triggered to generate relevant information when a clinician pushes a button on an identification tag or interacts in some way with the clinician-dashboard display device. In one aspect of the invention, the clinician dashboard component 312 automatically generates relevant information when a clinician walks into the room by use of the sensor interface 322. In yet another aspect, the clinician dashboard component 312 is triggered to generate relevant clinical information by voice command or by the performance of a defined gesture. In addition, in one aspect, the clinician-dashboard display device automatically shuts down upon determining that the clinician is no longer in the room. Any and all such variations, and any combination thereof, are contemplated to be within the scope of embodiments of the present invention.

The clinician-dashboard display device may be a monitor(s) positioned strategically in a smart clinical care room, or it may be a handheld device (laptop, tablet PC, PDA, mobile device, etc.). In one aspect, at least one of the monitors is positioned in a clinician zone so that a clinician can view the patient and the monitor at the same time. The positioning of the clinician-dashboard display device in the clinician zone enables the patient to view the monitor along with the clinician. This helps to draw the patient into the healthcare process instead of just having the patient being a passive recipient of care.

In another aspect, the clinician-dashboard display device is located on a foot wall in a patient zone so that the patient can view the clinician-dashboard display device while in bed. The clinician dashboard component 312, in one aspect, presents a graphical user interface configured to receive patient questions regarding care when the clinician is not present in the hospital room. When the clinician is later present in the room, the clinician dashboard component 312 generates a display with the questions so that the patient and the clinician can go through the questions together—a process that also helps make the patient an active participant in the healthcare process.

The patient interactive station component 314 manages a set of modules and GUIs that are related to the modules and are displayed on a patient interactive station. The general purpose of the modules and the patient interactive station is to provide the patient and the patient's family with access to components to make the patient's stay at the hospital more enjoyable. The modules include an information module for providing the patient or the patient's family with information about the healthcare facility. For instance, the information module provides information such as a mission statement of the healthcare facility, a welcome video, or a list of amenities available to the patient. Information module also provides maps and other directional information to enable patients to find their way around the healthcare facility. Additionally, the information module may provide patients with information about the geographical area surrounding the healthcare facility, such as local events and venues for food and lodging.

A care team module provides the patient or the patient's family with information about the clinicians designated to care for the patient throughout the patient's stay at the healthcare facility. For example, the care team module provides information such as the name, position, picture and personal and professional biography of clinicians that interact with the patient during the hospital stay. The care team module is also associated with an indoor positioning system to track the physical locations of the clinicians. Additionally, the care team module in association with the indoor positioning system enables a patient to request biography information about a clinician based on the clinician's name or picture. This information, in turn, may be displayed when the clinician enters the patient's room.

An education module provides the patient with health education information. For instance, the education module enables the patient to retrieve electronic documents from, for example, EMR 304, related to the patient's illness or course of treatment. Alternatively, the education module provides interactive education tutorials for the patient. The education module, via the patient interactive station component 314, may also keep track of when a patient has completed a health education information learning activity such as retrieving an electronic document or completing an interactive tutorial. In one aspect, an alert is sent to the patient's nurse when the patient has completed a learning activity, and the nurse can complete needed follow-up with the patient to make sure the patient understands the educational materials.

A scheduling module provides the patient with a representation of specific events and/or a task list for the day. The events populated on the patient's schedule may include scheduled tests, standard food service times, chapel services, and hospital events. In addition to the scheduled events, the scheduling module provides the patient with a patient-specific task list. For example, the task list may include instructions for the patient related to treatment or education such as designated patient education tutorials and required or recommended exercises.

A health records module enables the patient to access information regarding personal care. For example, the health records module may enable the patient to access portions of the patient's personal health record and update pertinent information. The health records module, via the patient interactive station component 314, accesses the healthcare facility's records keeping system (i.e., the EMR 304) and determines via parameters set by a clinician, the portions of a patient's EMR 304 accessible by the patient. The health records module may also allow the patient to edit select portions of the EMR 304 associated with the patient. For example, the health records module may enable a patient to update information relating to allergies or update emergency contact information. Additionally, the health records module may allow the patient to communicate with the patient's physician or member of the clinical care team.

A treatment module provides real-time information from medical devices associated with the patient. For example, the treatment module retrieves the information from a bus, the medical device interface 320, the connectivity engine 310, or from data published from the medical device interface 320 to the EMR 304.

A feedback module allows patients to provide real-time opinion information regarding their stay at the healthcare facility. The feedback module solicits input from the patient via quality of care surveys. The feedback module may include instant feedback notices to allow clinicians and the healthcare facility to take immediate action regarding an issue and work to improve the overall patient experience. The notification component of the feedback module may include an escalation and relay measure, which alerts the clinicians when the results of a patient feedback survey fall below a satisfactory level. The feedback module allows the management of the healthcare facility to target specific areas for feedback regarding new protocols or processes. The feedback module eliminates the delays often associated with standard written survey results.

An environmental module allows the patient, a clinician, or the patient's family members and/or friends to control the environmental conditions of the patient's room. For instance, the environmental module enables the patient to adjust the lighting setting in the room. Alternately, the environmental module allows the patient to control the temperature of his or her room. In one aspect, the environmental module automatically adjusts the lighting settings and/or temperature settings in the room in response to a triggering event. For example, upon initiation of a code blue event, the lights may be brought to full illumination above the patient's bed.

The set of modules also includes a television module, a gaming module, a movie module, a music module, an aromatherapy module, a menu module, and a scene module. The television module provides television services to the patient and/or the patient's family and friends. For example, the television module facilitates the patient's ability to pause/rewind or record live television. Additionally, a clinician and/or a parent of the patient may control, via the television module, the times when television services are available to the patient and the type of programming accessible by the patient. Further, the television module facilitates the patient's and or clinician's ability to modulate the acoustic output from the television and/or turn the television on or off. In one aspect, the television module automatically adjusts the acoustic output and/or the power in response to a triggering event.

The gaming module provides an interactive gaming experience for the patient. For example, the gaming module facilitates gaming though externally connected gaming systems of built-in computer-based games. The movie module provides movies to the patient. The movie module may provide the movies upon demand. As with the television module, a clinician and/or a parent of the patient may control via the movie module the times when movies are available to the patient and the type of movie content accessible by the patient.

The music module provides music upon patient demand. The music module provides a music library that can be accessed via the patient interactive station component 314. Clinicians may control via the music module the times when the patient is allowed to access the music content. For instance, patients may be prohibited from accessing music content during scheduled quiet periods. Further, the music module may automatically adjust the acoustic output in response to a triggering event. The aromatherapy module provides patients with a variety of aromatherapy scents to enhance patient well-being. In turn, the menu module provides patients with access to the food service system of the healthcare facility as well as restaurants associated with the healthcare facility. The menu module may also provide access to gift shops associated with the healthcare facility.

The scene module provides the patient with the ability to initiate a variety of scenes in a smart clinical care room (i.e., the smart clinical care room 200 of FIG. 2). A scene is a combination of room settings that help to facilitate a real-world activity. By way of illustrative example, a patient may select a reading scene, a television watching scene, a relaxation scene, and the like. In one aspect, the scene module interacts with any of the other modules of patient interactive station component 314 (i.e., the television module, the environmental module, the gaming module, the aromatherapy module, etc.), any of the other components of the smart room service 302, and/or the EMR 304 to initiate the requested scene. In addition, in one aspect, the scene module controls a digital ceiling and/or a digital window located in the smart clinical care room so that the display from the digital window and/or ceiling corresponds to the requested scene. The concepts of scenes will be explored more fully below with respect to FIGS. 4A-4C and FIG. 5.

The patient interactive station is located where the patient can most easily interact with it (i.e., proximate to a patient in a patient zone of a room). For example, in one aspect, the patient interactive station is located on the foot wall; while in another aspect, it is located on a monitor beside the patient's bed or attached to the patient's bed. Interaction with the patient interactive station may be by touch. For example, the patient can touch the actual screen of the patient interactive station to make a selection. In another aspect, the patient is provided with a pillow speaker that allows interaction with the patient interactive station. In yet another aspect, the patient is provided with a small touch screen tablet to interact with the patient interactive station. Voice commands and predefined gesture recognition may also be used to interact with the patient interactive station. In one aspect, gesture recognition is used in conjunction with the education module. By way of illustrative example, a physical therapy order exists in the EMR 304 regarding the patient. The patient interactive station component 314 communicates with the EMR 304 and generates for display a set of physical therapy exercises. The exercises are displayed on the patient interactive station, and gesture recognition technology is utilized by the patient interactive station component 314 to document that the patient is performing the physical therapy movements correctly.

The bed interface 316 is configured to receive inputs and send out instructions to a patient bed located in a patient zone, and interface with the other components of the smart room service 302. In addition, the bed interface 316 may also interface with the EMR 304. By way of example, the bed interface 316 captures information generated by the bed related to vital sign monitoring, moisture detection, weight detection, and the like, and stores this information in the EMR 304. The bed interface 316 automatically and without human intervention adjusts the bed to any number of positions in response to certain inputs to facilitate caring for the patient. For example, the head of the bed is adjusted to a certain angle upon receiving an indication that the patient is at risk for hospital-acquired pneumonia or ventilator-acquired pneumonia. In addition, the bed interface 316 may generate alerts to the clinical care staff if, for example, the head of the bed falls below a certain angle and the patient is at risk for pneumonia or has a diagnosis of pneumonia. The bed interface 316 may also automatically adjust the bed in response to certain triggering events which will be discussed in greater depth below.

The interactive room link component 318 receives inputs and communicates with room signage located outside the entrance to a smart clinical care room (i.e., in the pre-room entrance zone 210 of FIG. 2). In one aspect, inputs are received by the interactive room link component 318 via a touch screen on the room signage, a mobile application, verbal or gesture interaction with the room signage, or by some other attribute present in the smart clinical care room such as, for example, the patient interactive station. The interactive room link component 318 may generate for display by the room signage pertinent updates as clinician orders are received. By way of illustrative example, if an order is written restricting access to food in preparation for surgery, the room signage displays a message indicating that the patient is not allowed to have any food. This effectively notifies clinical care team members, hospital staff, as well as family and friends of the patient that the patient is not allowed to have food.

In another aspect, the patient or the patient's family can push messages out to the room signage via the interactive room link component 318. For example, the patient generates a message using, for example, the patient interactive station. This message is communicated to the interactive room link component 318 and subsequently displayed on the room signage. For example, the patient posts a message that the patient is visiting the gift shop and will be back shortly.

In another aspect of the invention, the interactive room link component 318 receives inputs indicating that the healthcare facility's transport service is transporting the patient. For example, the transport service indicates start and stop times of the transporting process by interacting with the room signage or by inputting the start and stop times on a mobile application. As well, housecleaning services also indicate start and stop times of the cleaning process by interacting with the room signage, or via a mobile application. Although not detailed here, many examples exist where the interactive room link component 318 receives inputs or generates outputs related to a clinician, patient, or hospital staff.

With respect to the medical device interface 320, a clinician may wish to associate a patient and at least one medical device via the medical device interface 320. In other words, the medical device interface 320 provides the needed link between a clinician, a medical device, and a patient. This association between the medical device and the patient allows the clinician to continually receive data from the associated medical device for as long as it is associated with the patient. This continuous feed of data may be fed from the medical device to the medical device interface 320 and on to other components/interfaces of the smart room service 302. The data is then sorted, and routed to the appropriate services and applications, such as a patient-to-device association application. Medical devices include any devices or mechanisms that may be used by a patient during a hospital stay. These medical devices may include a patient bed, monitors (e.g., fetal monitors), pumps (e.g., infusion pump), cardiac ventilators, sequential compression devices, electronic security devices, pharmacy dispensing stations, and the like. Further, the association of a patient to a medical device may continue until the occurrence of a disassociation event, which will be described below. The association continues not only when the medical device is in a smart clinical care room, but may continue for an extended period of time until a disassociation event occurs.

The medical device may be associated with the patient via the medical device interface 320 using patient identification information including, but not limited to, the patient's name, gender, date of birth, identification number, and the like. There are many ways to identify a patient. For instance, a patient may be identified by scanning a barcode that is located on or near the patient. When a patient is admitted to a hospital the patient may wear a wristband that has a barcode such that the patient may be easily identified. Alternatively, a patient's bed may have the patient's identification located somewhere on it for quick access. Another form of identification may be used instead of a barcode, such as a patient identification number or other identification form that may be entered into a mobile computing device (e.g., PDA or mobile PC) to identify the patient.

Another option for identifying a patient may include searching a database for a specific patient. The database may include each patient who is currently admitted to the hospital and thus any patient who is admitted to the hospital may easily be found in the database.

As mentioned above, the connectivity engine 310 displays any medical devices that have been identified and/or associated to the patient. Medical devices are identified in many of the same ways that patients are identified. For example, a barcode located on or near a medical device may be scanned, and information corresponding to that medical device may be uploaded to a mobile or portable computing device for display. Or, an identification number or other identifier corresponding to the medical device may be entered, either manually or electronically, to a portable computing device, for example. Alternatively, a search function may allow a clinician to search for a specific medical device that is located in a database even if that medical device is not associated with the identified patient. RFID tags may be associated with devices or patients.

Embodiments of the present invention allow a clinician to disassociate medical devices that are currently associated to a patient. In one aspect, a clinician may select specific medical devices, and select a disassociate button, and the selected medical devices will be disassociated from the patient. For example, upon a patient checking out of a hospital to return home, the medical devices that had been used to treat the patient, and, thus, had been associated to the patient, may be disassociated by the method described above. There are other ways that medical devices may be disassociated from a patient. For instance, the medical device may become disassociated by a patient when another patient becomes associated with that same medical device. This override may take place when a clinician is presented with a dialog box that indicates to the clinician that another patient is associated with that medical device. The clinician may have the option, in some embodiments, to override the existing association.

Sensor interface 322 communicates with sensors and/or identifiers located not only in a smart clinical care room, but throughout the healthcare facility in which the patient is located. The sensor interface 322 tracks the location of identifiers in the healthcare facility and receives information and inputs emitted from the sensors. The sensors and/or identifiers may utilize ultrasound technology, infrared technology, radio-frequency identification (RFID) technology, or the like. Identifiers are worn by clinicians, patients, and/or family members and may take the form of a security badge, an item attached to a security badge, or the like. Sensors are located at fixed intervals in the healthcare facility including the patient room.

Signals are transmitted by the sensors and are received by the identifiers. The identifiers respond to the signals. A response from an identifier is received by the sensors and communicated to the sensor interface 322. The sensor interface 322 recognizes and determines the location and identity of the responding identifier. For example, when a clinician identifier is identified by the sensor interface 322, the location for the clinician associated with the clinician identifier is updated. The information concerning the location of the clinician may be shared with the patient and/or the patient's family. In one aspect, the sensor interface 322 communicates the information to the interactive room link component 318, and the location information is displayed on the room signage. In another aspect, the location information is displayed on a patient interactive station associated with the patient interactive station component 314.

The sensor interface 322 may also be utilized to optimize a clinical experience for a patient or an individual associated with the patient, such as a family member. The clinical experience is often overlooked for the individuals associated with the patient. Many times, family members sit with a patient for endless hours to avoid leaving the patient's side and missing an important clinical event without ever being notified of an opportunity to be included in the clinical event. Embodiments of the present invention seek to alleviate the stress on the patient and the patient's family.

Privacy regulations provide that patient information may not be shared with unauthorized individuals. Thus, embodiments of the present invention are applicable to one or more individuals that are approved by the patient to receive notifications of clinical information. The individual receiving the clinical information must also enable a computing device to receive the clinical information. Any web-enabled computing device may receive clinical information. The clinical information may be received in the form of a notification and/or message.

By way of example only, assume that a non-present party (e.g., a family member) has left the patient's room to go to a vending machine. The non-present party would like to be notified if the patient's clinician is near the patient. A mobile computing device may receive such a notification, and the non-present party can return to the room to speak with the clinician.

The non-present party may be tracked via an identifier in the same way as patients and clinicians are tracked. The present invention may also include predefined location stations to aid navigation such that it is not necessary that a non-present party be tracked. The non-present party may simply identify their location at the location station and utilize the present invention in the same way as if they were being tracked. If the non-present party is presented with turn-by-turn directions, then the steps will update upon receiving an indication from the user to present the next step. Alternatively, the non-present party could be tracked via a plurality of sensors and the directions may automatically update as the non-present party's location is updated from passing a sensor.

The communication component 324 is configured to communicate with communication devices used within a healthcare facility to receive and send information. The communication component 324 is also configured to receive requests for additional information and to communicate with other components and/or interfaces of the smart room service 302. Exemplary communication devices include personal communication devices, a workstation, a nursing station, a nurse call system, an intercom system, and an email system.

Personal communication devices include devices that are used by an individual to receive and send information, such as an in-house phone, a pager, and a mobile device. A workstation includes a remote computer terminal that is used to present information to clinicians and receive inputs from clinicians. A workstation might be set up at a nurse's station to or at a patient's bedside. A nurse call system includes communication devices that present information to and receive information from a nurse (or other healthcare professional). An intercom system includes communication devices that receive and announce information by utilizing, for example, speakers. An email system might be implemented using one or more of the other communication devices (for example, a personal communication device, or a workstation) to send and receive messages (e.g., email messages, SMS messages, etc.) to various users.

Accordingly, in an embodiment of the present invention, the communication component 324 presents information to clinicians using one or more of the communication devices outlined above. The information may be received by the communication component 324 from other components and/or interfaces of the smart room service 302. For example, the communication component 324 may receive information concerning a medical device via the medical device interface 320 or the connectivity engine 310 and communicate this information to a nurse call system, or a personal communication device. Moreover, the communication component 324 might also generate information (e.g., code-blue alert) that is communicated to other components of the smart room service 302. As well, the communication component 324 is configured to communicate to other components of the smart room service 302 requests to receive additional information. For example, a personal communication device might communicate a request of a physician to receive information from the EMR 304.

The zones and components discussed above with respect to FIGS. 2 and 3 are used to transition a smart clinical care room (i.e., the smart clinical care room 200 of FIG. 2) from a first scene to a second scene. The transition from a first scene to a second scene can be in response to some triggering event. The triggering event may be a manual trigger by a clinician, a patient, or a family member or friend of the patient. In another aspect, the triggering event is an automatic trigger upon detection of certain information. In one aspect of the invention, the second scene facilitates completion of the real-world activity. A real-world activity comprises physical involvement with one or more people to realize a tangible goal. A person may use a computing device or machine to complete the real-world activity, but the real-world activity is not solely performed by a computing device. The transition to a scene that facilitates completion of the real-world activity can be accomplished by a computing-device alone, without human interaction. One or more of the zones discussed above, along with a smart room service (i.e., the smart room service 302 of FIG. 3), are utilized to transition from a first scene to a second scene. FIGS. 4A-4C and FIG. 5 provide some illustrative examples of types of scenes contemplated to be within the scope of the invention. The arrangements shown in FIGS. 4A-4C and FIG. 5 are merely exemplary and are not meant to be limiting in any way.

Figure 4A:
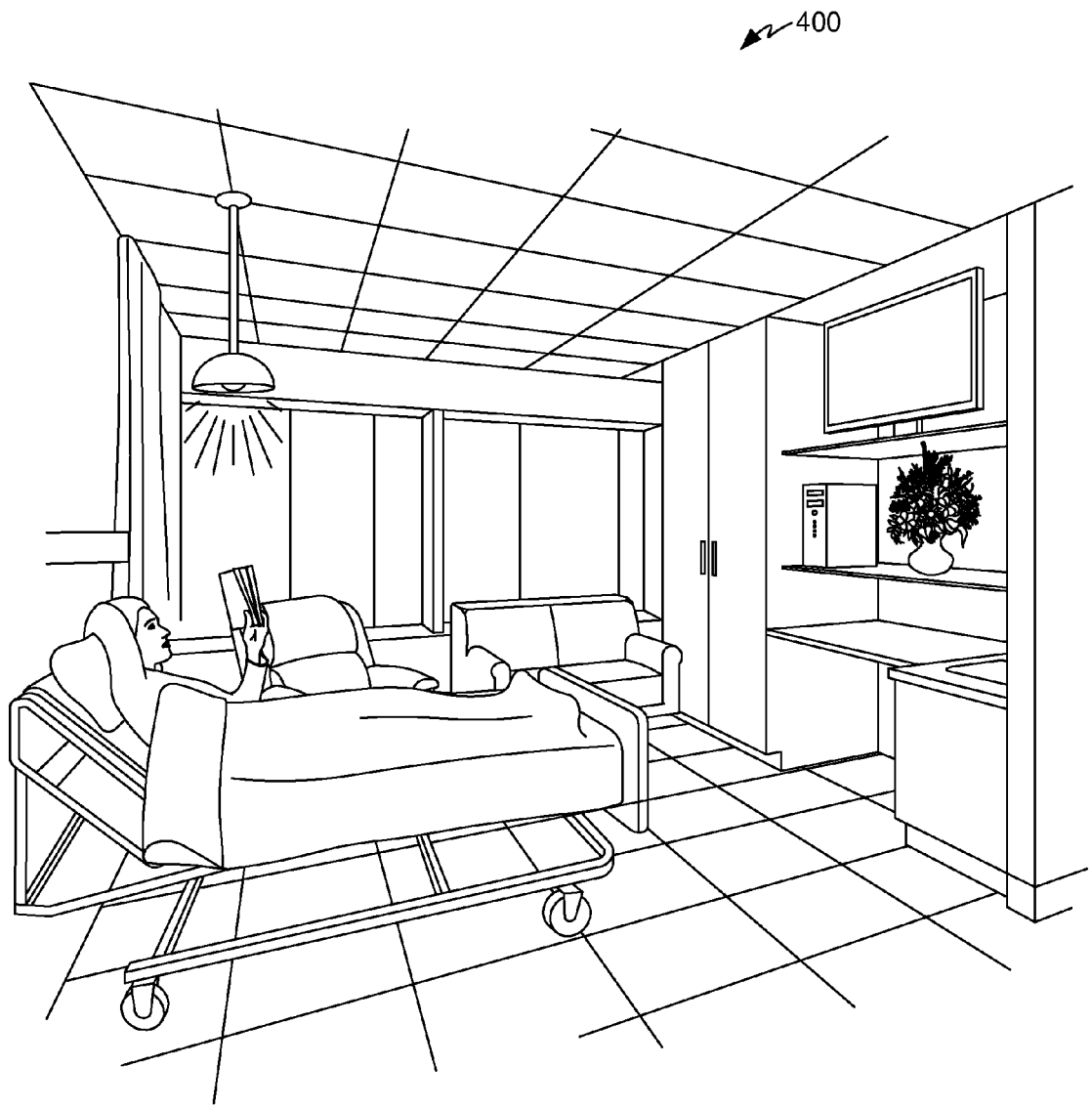
FIGS. 4A-4C depict exemplary scenes associated with a smart clinical care room suitable to implement embodiments of the present invention.

FIG. 4A depicts a reading scene and is referenced generally by the numeral 400. In one aspect, a patient, or a visitor of the patient, in a smart clinical care room interacts with, for example, a patient interactive station to request a reading scene. In another aspect, the patient interacts with some other component of a smart room service (i.e., the smart room service 302 referenced in FIG. 3) to request a reading scene. Upon receiving the request for the reading scene, the smart clinical care room is automatically and appropriately illuminated, acoustic outputs are automatically minimized, and the patient bed is automatically adjusted to a position that facilitates reading. For example, the head of the bed is adjusted to elevate the upper half of the patient's body. In another aspect of the invention, a friend or family member of the patient interacts with the patient interactive station to request a reading scene for the friend or family member. In this instance, the family zone of the smart clinical care room is illuminated and acoustic outputs minimized. Any and all such variations, and any combination thereof, are contemplated to be within the scope of embodiments of the present invention.

Figure 4B:
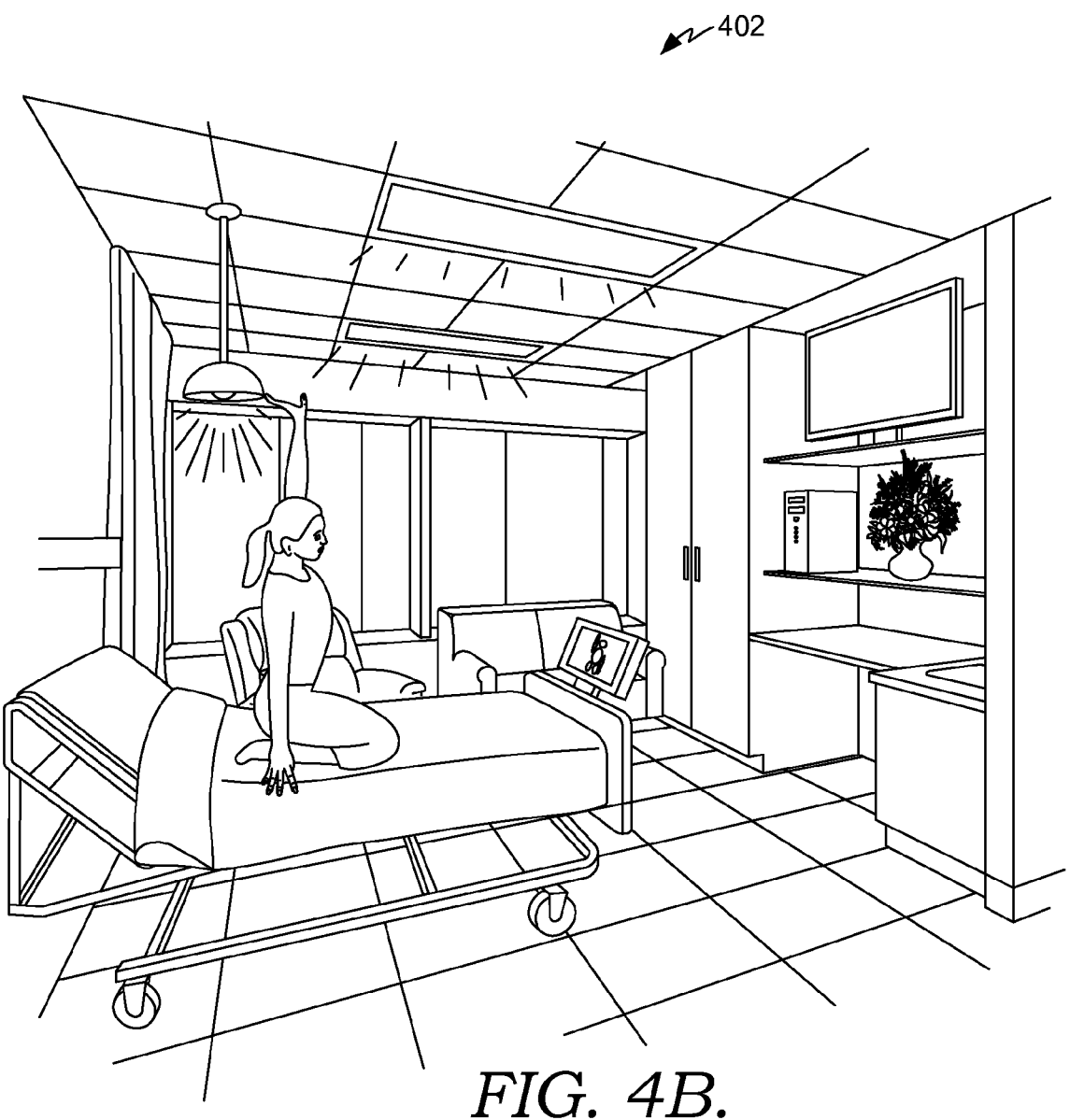

FIG. 4B depicts a physical therapy scene and is referenced generally by the numeral 402. A smart room service may receive an indication that communicates the patient is ready to begin a physical therapy session. Such an indication could be received from a clinician or from the patient. By way of illustrative example, the patient interacts with a patient interactive station, or the clinician interacts with a clinician-dashboard display device. In another aspect, the smart room service accesses the physical therapy order through an electronic medical record (i.e., the EMR 304 of FIG. 3). Incident to receiving this indication, the room is illuminated in order to facilitate the physical therapy session, acoustic outputs are adjusted so that there is minimal sound in the room, and the bed is adjusted to facilitate the patient's physical therapy, the type of adjustment is dependent upon what type of physical therapy movements are prescribed. In addition, a physical therapy module is displayed on a monitor positioned so that the patient can both view the monitor and perform the physical therapy movements. In one aspect of the invention, gesture recognition technology is utilized to ensure the patient is performing the physical therapy movements correctly. If, for example, it is detected that a movement is not being performed correctly, the physical therapy module initiates a training module to help the patient learn the correct movement. Any and all such variations, and any combination thereof, are contemplated to be within the scope of embodiments of the present invention.

Figure 4C:
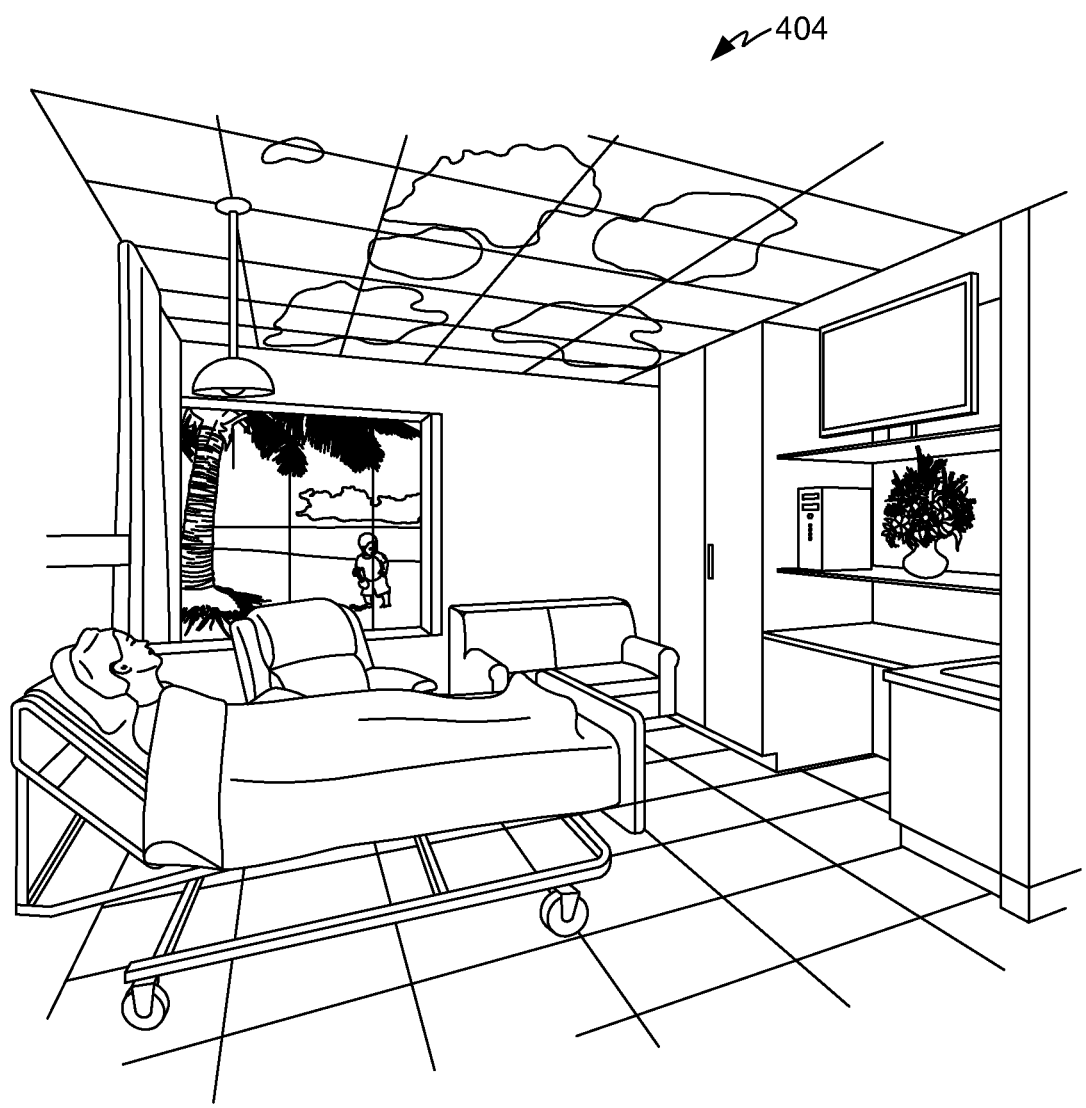

FIG. 4C depicts a relaxation scene and is referenced generally by the numeral 404. An indication is received by, for instance, a smart room service (i.e., the smart room service 302 referenced in FIG. 3) that a relaxation scene is desired. For example, the indication is received from a clinician, the patient, or a member of the patient's family and occurs through interaction with, e.g., a patient interactive station or a clinician-dashboard display device. Upon receiving the indication, a digital ceiling and/or window in a patient room is set to scenery that evokes a relaxed state of mind, illumination in the room is dimmed, soothing music is played, aromatherapy initiated, and a patient bed in the room is set to a position that facilitates relaxation. For example, the head of the bed may be adjusted so that the patient's upper body is slightly elevated. Any and all such variations, and any combination thereof, are contemplated to be within the scope of embodiments of the present invention.

Figure 5:
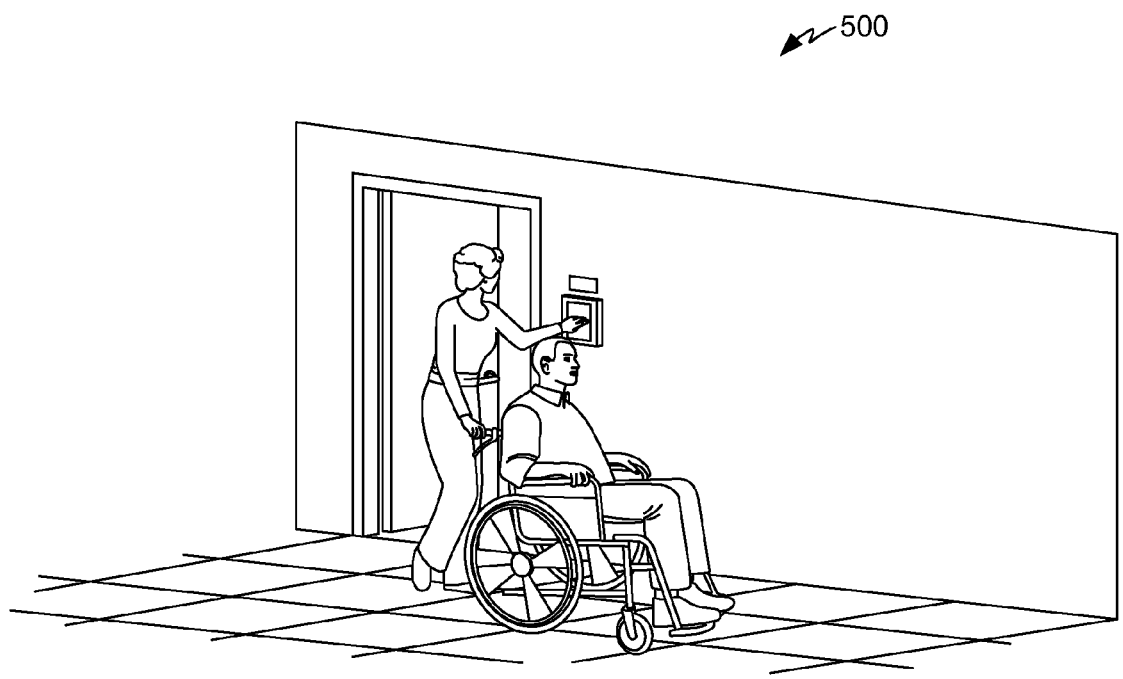
FIG. 5 depicts an exemplary scene associated with a smart clinical care room suitable to implement embodiments of the present invention.

FIG. 5 depicts a transport scene and is referenced generally by the numeral 500. The transport scene may be triggered, for example, upon a smart room service (i.e., the smart room service 302 of FIG. 3) receiving an indication from a clinician that the patient needs to be transported to a specified location in the healthcare facility. For example, an order is entered, stored in an electronic medical record (i.e., EMR 304 of FIG. 3), and communicated to the smart room service. In one aspect of the invention, a transporter receives an indication (for example, by receiving a notification via the communication component 324 of FIG. 3 on a mobile device) that a patient in a smart clinical care room needs to be transported. After assisting the patient into a wheelchair, the transporter interacts with, for example, the room signage upon leaving the room with the patient. Incident to this interaction, lights and televisions in the room are turned off, an indication that the patient is being transported is displayed on the room signage, and clinicians and family members are notified that the patient is in transport and is not present in the room. Upon returning to the smart clinical care room with the patient, the transporter again interacts with the room signage to indicate that the patient has returned to the room. Incident to this interaction, the room lights and television are adjusted to pre-transport levels, the room signage displays a message indicating the patient is in the room, and clinicians and family members are notified (via, for example, the communication component 324 of FIG. 3) that the patient is back in the room. FIGS. 4A-4C and FIG. 5 are representative examples of the many scenes that may be initiated in the smart clinical care room 200.

Figure 6:
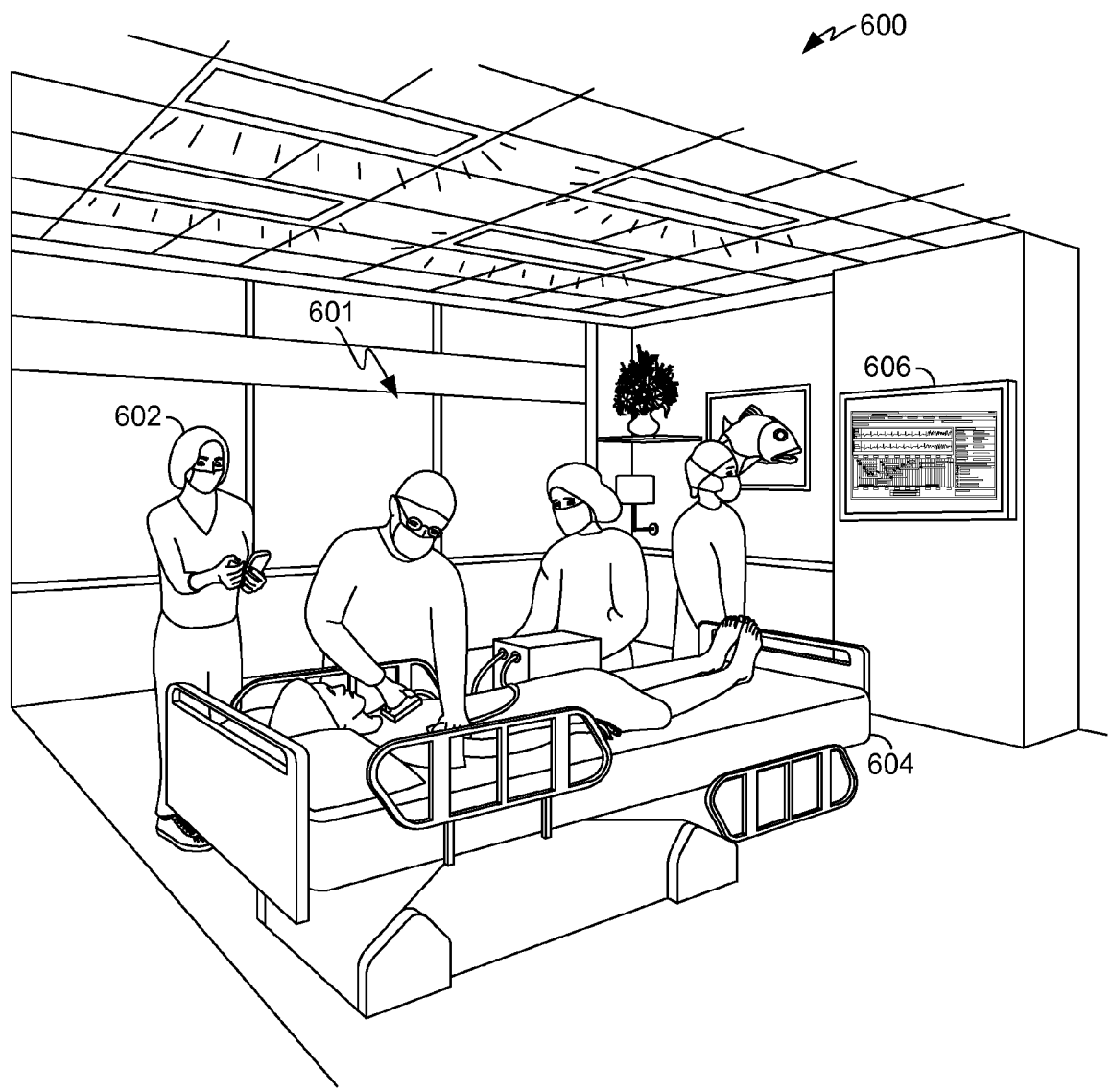
FIG. 6 depicts an exemplary code blue scene associated with a smart clinical care room suitable to implement embodiments of the present invention.

One scene that is of critical importance in a healthcare setting is a code blue scene. This scene is depicted in FIG. 6 (referenced generally by the numeral 600) and will be explained in greater depth below. The term code blue as used in this application refers to a patient experiencing cardiopulmonary arrest. The successful management of a code blue event requires quick detection of the code blue event, rapid response times by a code blue team, knowledge of code blue protocols, coordination of the code blue team, and accurate documentation of clinical events that occur during the code blue event. The smart clinical care room is designed to meet these needs through the use of the zones and the components present in the room.

In one aspect of the invention, a code blue alert is activated via voice, touch or gesture and recognized by, for example, a clinician dashboard display device or a patient interactive station. In another aspect, a code blue alert is automatically activated upon detection of a triggering event by a patient monitoring device such as, for example, a cardiac arrhythmia, asystole, pulmonary arrest, and the like. In one aspect, upon activation of the code blue alert, a clinician responsible for the patient is notified; the clinician would check the patient and initiate a full code blue alert if the code blue event is verified. In another aspect of the invention, a code blue team (referenced by the numeral 601 in FIG. 6) is automatically notified when the code blue alert is activated. The team 601 may be notified, for example, by a notification sent to one or more mobile devices associated with the code blue team 601. The notification includes information about the patient such as, for example, name and location in the healthcare facility.

Upon triggering of the code blue event, a dome light outside the room entrance is illuminated and the room signage displays a message indicating a code blue occurrence. Both of these measures allow the code blue team members 601 to quickly identify the room in which the code blue event is occurring which decreases response times. Acoustic outputs are minimized in the room by, for example, powering off any televisions that are on, and turning off any music that is playing. Referring to FIG. 6, the room is brought to full illumination. Furniture in the family zone may automatically fold up to help clear space for the code blue team members 601 upon determining that no one is sitting on the furniture. In essence, the smart clinical care room is effectively converted to one large clinician zone. A patient bed 604 in FIG. 6 is automatically positioned to a code blue position upon determining that the patient is securely on the bed. For example, a bed interface (i.e., the bed interface 316 of FIG. 3) determines that the patient's weight is substantially below a recently documented weight for the patient. Such determination prevents the bed from being automatically adjusted to a code blue position. In addition, a crash cart may be associated with the patient.

In one aspect of the invention, a clinician dashboard component (i.e., the clinician dashboard component 312 of FIG. 3) generates for display by a clinician-dashboard display device a code blue team view 606 where the team view can be seen by all members of the code blue team 601. The code blue team view 606 can be in the form of a GUI. The code view team view 606 displays clinical event information in near real-time. The clinical event information is automatically captured, or manually inputted. By way of illustrative example, the clinician dashboard component captures information from any of the components present in the smart clinical care room. As well, the clinician dashboard component captures information that is being manually documented by a member of the code blue team 601 that is in charge of documentation, hereinafter known as the documenter. The documenter is indicated by the numeral 602 in FIG. 6.

Figure 8:
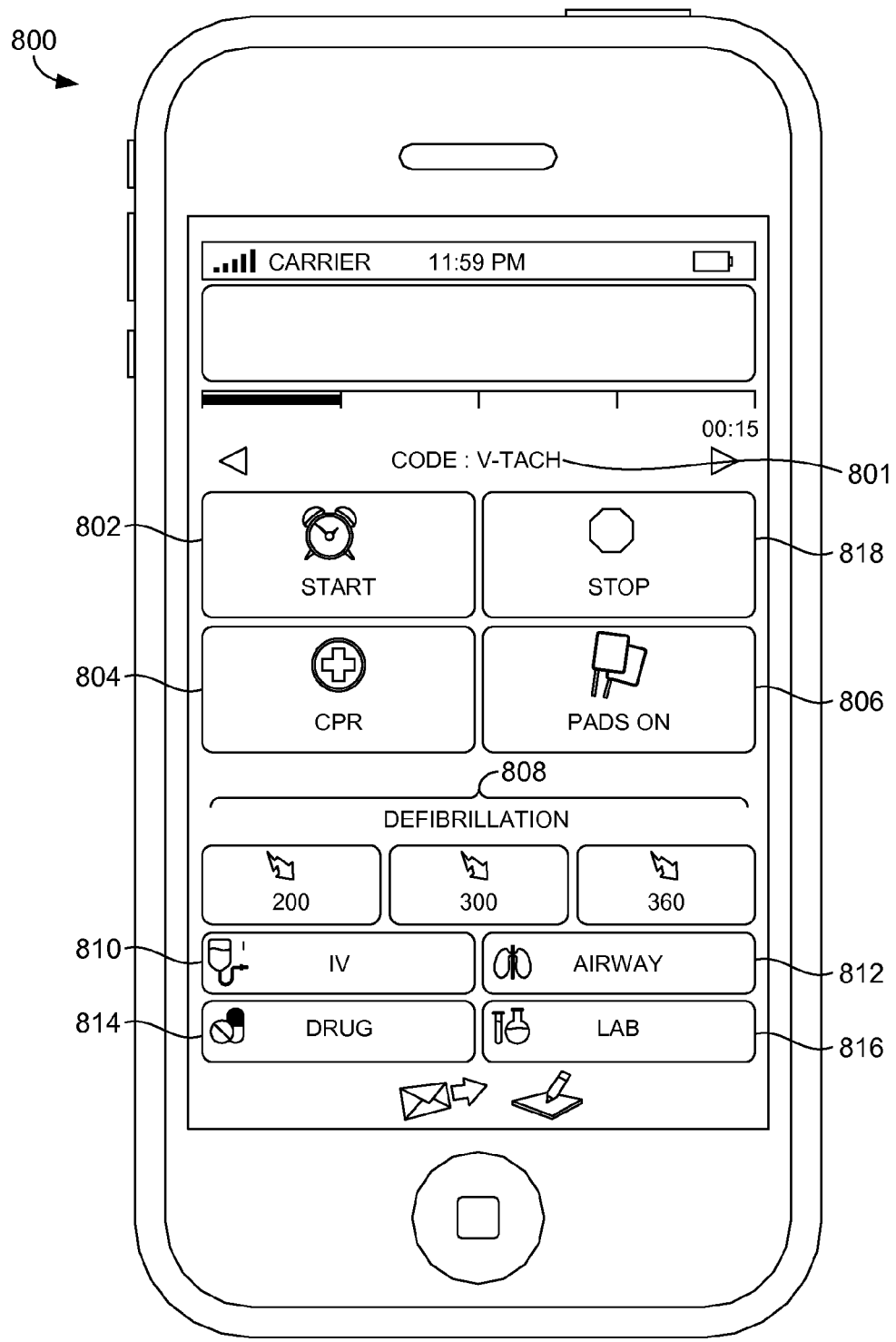
FIG. 8 depicts an exemplary graphical user interface of a device associated with a code blue event suitable to implement embodiments of the present invention.

FIG. 8 depicts an input device that is used by the documenter 602, referenced generally by the numeral 800, to record clinical event information during the code blue event. In one aspect, the information is inputted via an application on a mobile device. With respect to FIG. 8, the documenter 602 may input a medical condition 801 that initiated the code blue event, such as, for example, ventricular tachycardia (V-Tach). A time 802 the code blue response begins is documented as well as a time 804 that cardio-pulmonary-resuscitation (CPR) begins. If the patient requires defibrillation, a time 806 at which the defibrillator pads are placed on the patient is noted, along with times and energy amounts 808 of shocks delivered to the patient. The documenter 602 is able to document any intravenous fluids 810 the patient may be receiving, the necessity or type of airway 812 that may be established for the patient, drugs 814 administered to the patient, and labs and lab results 816 drawn on the patient. In addition, the documenter 602 can also input a stop time 818 for when the code blue response is terminated.

As mentioned, the clinician dashboard component captures the information inputted by the documenter 602 along with clinical event information captured by other components in the smart clinical care room. For example, the clinician dashboard component captures identities of code blue team members 601 along with a time that the code blue team members 601 arrive in the room through communication with, for example, a sensor interface (i.e., the sensor interface 322 of FIG. 3). The use of sensors in the smart clinical care room enables monitoring of the movement of code blue team members 601 and equipment throughout the room. The use of sensors also allows a position in the room to be determined for each member of the code blue team 601. This may be important at a later point in time when quality measures are reviewed with respect to the code blue response.

The code blue team view 606 generated by the clinician dashboard component dynamically changes depending on the type of clinical event information received by the smart room service. Thus, code blue protocols can be dynamically updated depending on the results of, for example, labs drawn, medications delivered to the patient, shock treatments administered to the patient, and the like.

Figure 7A:
Figure 7B:
Figure 7C:
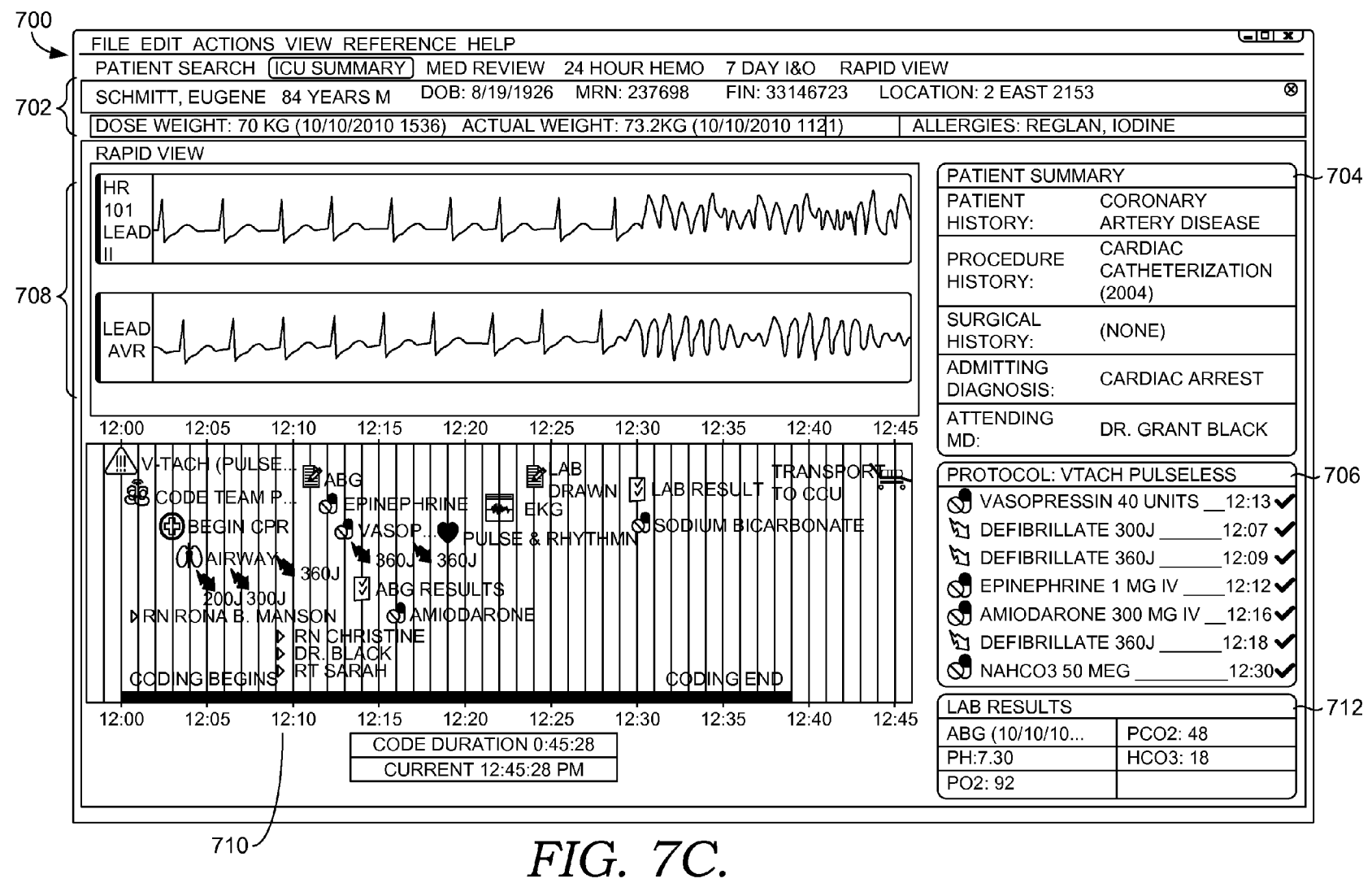

Turning to FIGS. 7A-7C, some exemplary depictions of GUIs generated by the clinician dashboard component during the code blue event are presented and are referenced generally by the numeral 700. FIGS. 7A-7C represent different times during the code blue event with FIG. 7A corresponding to the beginning of the code blue event, FIG. 7B the middle of the code blue event, and FIG. 7C corresponding to the end of the code blue event.

With respect to FIG. 7A, a general patient information area 702 contains general patient information such as, for example, patient name, patient identifier, date of birth, actual weight and dosing weight, and allergies. A patient summary area 704 includes such information as patient history, procedure history, surgical history, admitting diagnosis, and attending physician. This is just a sample of the many types of information that may be displayed in the patient summary area 704.

A protocol area 706 displays a continually updated protocol that is responsive to real-time inputs associated with the patient. In one aspect of the invention, the information displayed in the protocol area 706 includes a "suggested next care step based on patient response or incoming result." The suggested next step may be driven by a preset algorithm, a complex rules engine, or by a complex event processor monitoring transactional data from multiple sources. By way of illustrative example, the protocol area 706 initially displays a standard code blue protocol for a patient experiencing ventricular tachycardia. But as the code progresses, the heart rhythm switches from ventricular tachycardia to asystole (no heart beat). This change necessitates a completely different protocol from that used for ventricular tachycardia. Or, in another example, a lab result comes back that indicates that the patient's blood gases are outside of normal limits. The protocol area 706 dynamically changes to include unified protocol information that addresses the blood gas abnormality, the arrhythmia, and any effect the blood gas abnormality has on the arrhythmia. These are just a few of the many examples of how the protocol information updates in response to clinical event information. The protocol area 706 may also display an indication that a certain step in the protocol has been completed and a time at which it was completed.

An electrocardiogram area 708 is configured to display near real-time electrocardiogram (EKG) information associated with the patient, while a timeline area 710 displays a running timeline illustrating the clinical events that are happening with respect to the code. This information includes times at which various events occur such as, for example, a time the code blue event is initiated, a time the code blue team is paged, and a time at which various clinicians arrive in the room. In addition, the information includes the type of presenting arrhythmia and the identity of clinicians in the room. The timeline area 710 may also display a code duration time along with a current time. A lab results area 712 displays the results of labs as the information is captured by, for example, a clinician dashboard component.

FIG. 7B depicts the GUI 700 at a slightly later point in time. As can be seen in the timeline area 710, information concerning the identity and arrival of the code blue team members is documented, along with a time at which CPR was initiated, a time at which an airway was established, and when defibrillation occurred along with the energy amount of the shocks. The lab results area 712 also displays results of labs that were drawn on the patient during the code blue event.

FIG. 7C depicts the GUI 700 at a still later point in time. Besides depicting the type of information discussed above, the timeline area 710 depicts information concerning times and identities of medications administered to the patient, times at which labs were drawn, times at which lab results are received, times at which arterial blood gases were drawn and the results received, times at which a pulse and normal sinus rhythm are detected, a time when the coding protocol ends, and a time when the patient is transported to the cardiac care unit. In addition, the protocol area 706 has been updated to reflect new protocol information concerning the patient based upon responses to electrical shock, medications, and other therapeutic measures. These are just representative examples of the many types of information that can be displayed by the GUI 700. Any information pertinent to a code blue situation is contemplated to be within the scope of the invention.

At any time during the code blue event, a clinician can interact with the GUI 700. Such interaction may be via voice, touch, or gesture recognition. For example, the clinician may want to select an event occurrence on the display to access more information about that event. By way of illustrative example, the clinician touches or says the name of a medication in the timeline area 710 (i.e., vasopressin). Incident to this interaction, information is displayed concerning this medication such as dose administered, side effects, and the like.

In one aspect of the invention, an indication that the code blue event is over is triggered by a manual input. In response to the indication, the smart clinical care room transitions back to a pre-code blue scene. In one aspect of the invention, after the code blue event is over, a notification for restocking of the crash cart is automatically generated. In addition, because the crash cart was associated with the patient at the beginning of the code blue event, any charges for medications, supplies, etc. will automatically be generated and billed to the patient's account.

Figure 9:
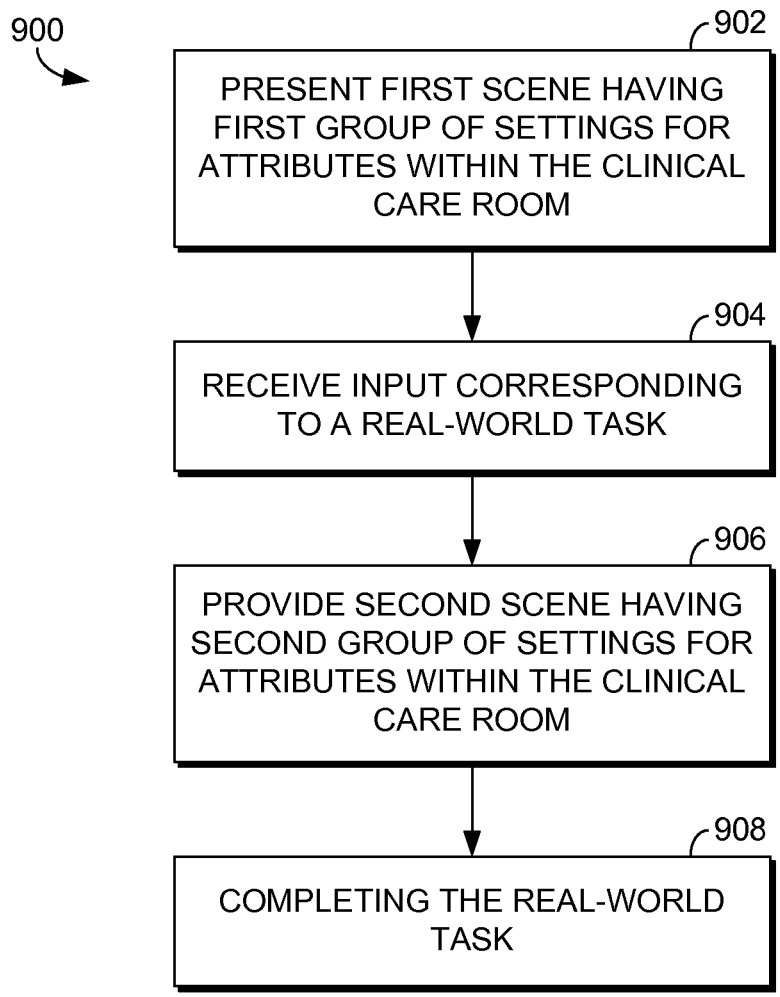
FIG. 9 depicts a flow diagram illustrating a method for transitioning a clinical care room from a first scene to a second scene in order to facilitate completion of a real-world activity suitable to implement embodiments of the present invention.

With reference to FIG. 9, a flow diagram is illustrated showing a method 900 for transitioning a clinical care room from a first scene to a second scene in order to facilitate completion of a real-world activity. At block 902, the first scene is presented in the clinical care room where the clinical care room has one or more zones. The first scene is associated with a first group of settings for components within the one or more zones. As mentioned above, the components may include any device or apparatus that impacts patient clinical care or manipulates the clinical environment in the clinical care room such as, for example, any of the components and/or interfaces of the smart room service 302 of FIG. 3. As well, the components may include any software module that provides instruction to other components. Components may also include such things as lights, television, sound system, furniture, and the like.

At block 904, an input corresponding to the real-world activity is received. As mentioned above, the input may be a manual input received from a clinician, patient, and/or family member through interaction with any of the components and/or interfaces of the smart room service, or through interaction with, for example, a patient interactive station or a clinician dashboard display device. Or the input may be an automatic input that is generated in response to a triggering event. For example, a patient monitoring device detects a heart arrhythmia and automatically generates an alert that is received as an input. The input received at step 904 corresponds to a real-world activity. There are a wide variety of examples of real-world activities, some of which were mentioned above. Some representative examples include reading, relaxation, entertainment, education, travel, personal hygiene, patient care, and the like.

At step 906, incident to receiving the input corresponding to the real-world activity, a second scene is provided. The second scene comprises a second group of setting for the components within the zones in the clinical care room. The second group of settings is different than the first group of settings. The second group of settings is optimized to facilitate completion of the real-world activity. For example, a second group of settings for a reading scene includes increasing the lighting level above a patient's bed, decreasing acoustic outputs, and positioning the bed to facilitate reading. At step 908, the real-world activity is completed.

Figure 10:
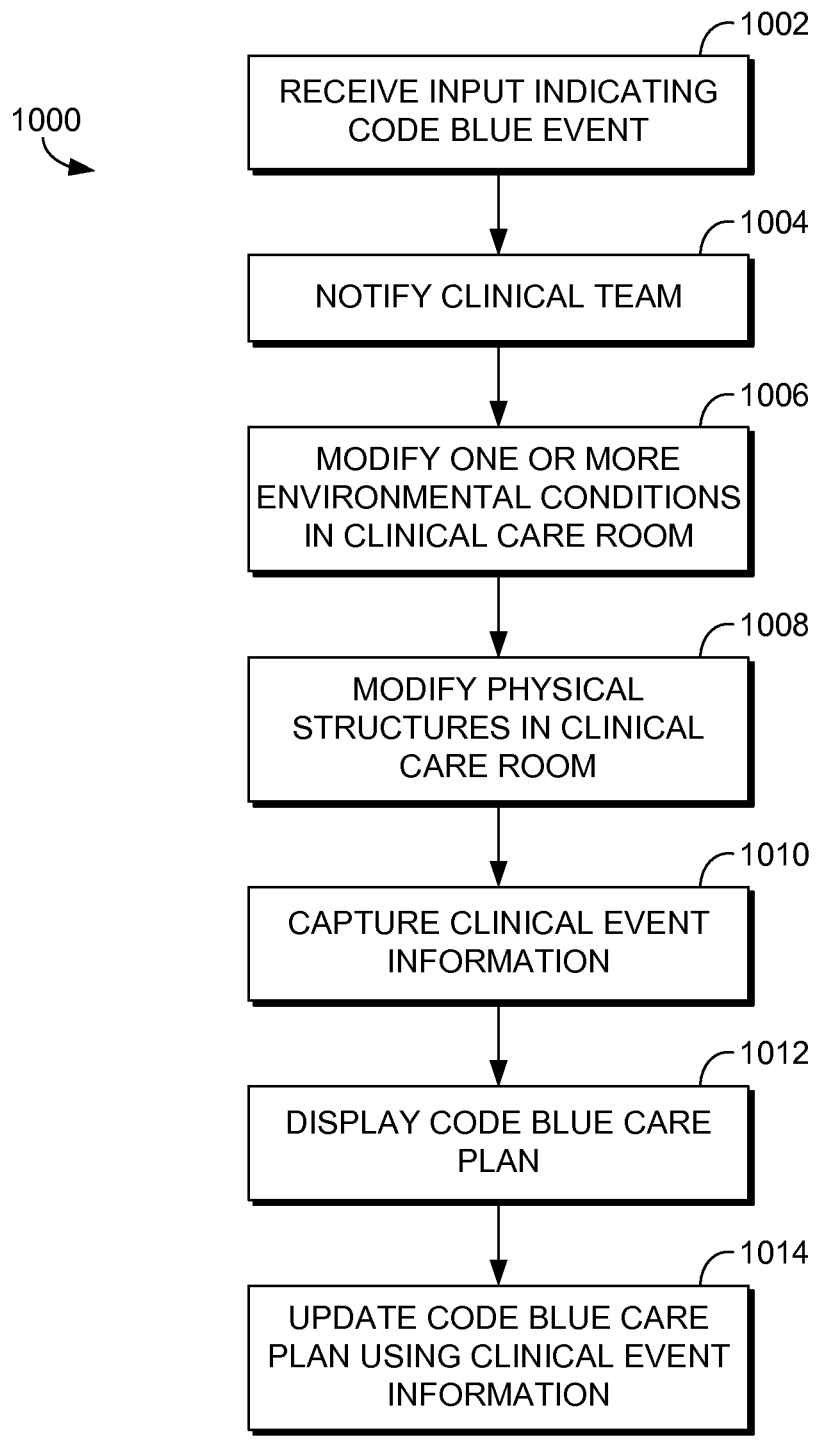
FIG. 10 depicts a flow diagram illustrating a method for adaptively utilizing a clinical care room to facilitate caring for a patient suitable to implement embodiments of the present invention.

With reference to FIG. 10, a flow diagram is depicted illustrating a method 1000 for adaptively utilizing a clinical care room to facilitate caring for a patient. At block 1002, an input is received indicating a code blue event has been initiated for the patient. At block 1004, a clinical care team is notified of the code blue event. At block 1006, one or more environmental conditions in the clinical care room are modified. One or more physical structures in the clinical care room are modified at block 1008. At block 1010, clinical event information relating to the clinical care room and the patient is captured. At block 1012, a code blue care plan is displayed to members of the clinical care team. The code blue care plan is updated using the captured clinical event information at block 1014.

The present invention has been described in relation to particular embodiments, which are intended in all respects to be illustrative rather than restrictive. Further, the present invention is not limited to these embodiments, but variations and modifications may be made without departing from the scope of the present invention.

The invention claimed is:

1. One or more non-transitory computer-readable storage media having embodied thereon computer-useable instructions which, when executed by a computing device, cause the computing device to perform a method for adaptively utilizing a clinical care room to facilitate caring for a patient, the method comprising:
receiving an input indicating the patient is experiencing a code blue event, wherein the code blue event comprises cardiopulmonary arrest;
incident to receiving the input:
(1) automatically and without human intervention notifying a clinical care team of the code blue event,
(2) automatically and without human intervention modifying one or more physical structures in the clinical care room to facilitate patient care including placing a patient bed in a predefined code blue position, powering off any television that is on, and transitioning a clinician-dashboard display device from a clinician view to a team view displaying a code blue care plan comprising one or more suggested next steps of care for the patient's cardiopulmonary arrest based on clinical event information,
(3) automatically and without human intervention capturing the clinical event information related to the clinical care room and the patient,
(4) automatically and without human intervention displaying the code blue care plan to the clinical care team, and
(5) utilizing the clinical event information to adaptively update the code blue care plan.

2. The media of claim 1, wherein the input indicating the patient is experiencing the code blue event is automatically generated upon detection of a triggering event by a patient monitoring device.

3. The media of claim 1, wherein the clinical care team is notified by communicating a message to one or more mobile devices associated with the clinical care team.

4. The media of claim 1, wherein the modifying one or more physical structures in the clinical care room further comprises fully illuminating the clinical care room.

5. The media of claim 1, wherein the clinician-dashboard display device is positioned so that it is viewable by members of the clinical care team.

6. The media of claim 1, wherein the capturing clinical event information related to the clinical care room and the patient comprises capturing automatic inputs and outputs and manual inputs and outputs.

7. The media of claim 1, wherein the capturing clinical event information related to the clinical care room comprises utilizing room sensors to capture signals emitted by radio-frequency identification tags worn by members of the clinical care team in order to document their presence and position in the clinical care room.

8. The media of claim 1, wherein the capturing clinical event information related to the clinical care room and the patient comprises at least one of the following: outputs from patient monitoring devices, medications administered to the patient, lab results, procedures performed on the patient, times at which clinical events occur, and transport events related to the patient.

9. The media of claim 1, further comprising:
automatically and without human intervention modifying one or more environmental conditions outside the clinical care room to facilitate patient care; and
automatically and without human intervention modifying one or more environmental conditions in the clinical care room to facilitate patient care.

10. The media of claim 1, wherein the code blue care plan is adaptively updated in real-time.

11. The media of claim 1, wherein an indication is received that the code blue event is terminated.

12. The media of claim 11, wherein the clinical care room automatically and without human intervention transitions back to its pre-code blue state incident to receiving the indication that the code blue event is terminated.

13. One or more non-transitory computer-readable storage media having embodied thereon computer-useable instructions which, when executed by a computing device, cause the computing device to perform a method for adaptively utilizing a clinical care room to facilitate caring for a patient experiencing a code blue event, the method comprising:
receiving an input indicating the patient is experiencing the code blue event, wherein the code blue event comprises cardiopulmonary arrest;
incident to receiving the input indicating the code blue event:
(1) automatically and without human intervention notifying a code blue team of the code blue event,
(2) automatically and without human intervention modifying one or more environmental conditions in the clinical care room to facilitate patient care by adjusting room lighting and adjusting acoustic outputs in the clinical care room,
(3) automatically and without human intervention modifying one or more physical structures in the clinical care room to facilitate patient care by adjusting a position of a patient bed,
(4) capturing event information related to the clinical care room and the patient, wherein the event information includes at least one of:
a) a presence and position of members of the code blue team,
b) a time at which clinical events occur,
c) medications administered to the patient,
d) lab results, and
e) procedures performed on the patient, and
(5) displaying a code blue care plan to the code blue team, wherein the code blue care plan comprises one or more suggested next steps of care for the patient's cardiopulmonary arrest based on the event information,
(6) utilizing the event information to adaptively update the code blue care plan, and
(7) displaying advice related to a next step in the code blue care plan.

* * * * *